United States Patent [19]

Morse

[11] 4,269,859

[45] May 26, 1981

[54] CELLULOSE FLOC GRANULES AND PROCESS

[75] Inventor: Erwin E. Morse, Berlin, N.H.

[73] Assignee: Brown Company, Kalamazoo, Mich.

[21] Appl. No.: 31,544

[22] Filed: Apr. 19, 1979

[51] Int. Cl.$^3$ .......................... A61K 9/20; A61K 47/00
[52] U.S. Cl. .................................... 424/362; 264/117; 536/56
[58] Field of Search .................. 424/362, 35; 264/117; 536/56

[56] References Cited

U.S. PATENT DOCUMENTS

| | | | |
|---|---|---|---|
| 1,729,629 | 10/1929 | Richter et al. | 536/56 |
| 1,935,579 | 11/1933 | Richter | 536/56 |
| 1,964,772 | 7/1934 | Schur et al. | 536/56 |
| 2,036,606 | 4/1936 | Richter | 536/56 |
| 2,182,274 | 12/1939 | Baker et al. | 536/56 |
| 2,618,018 | 11/1952 | Downing et al. | 536/56 |
| 2,663,907 | 12/1953 | Downing et al. | 536/56 |
| 3,278,383 | 10/1966 | White | 424/362 |
| 3,357,845 | 12/1967 | Battista | 536/56 |
| 3,564,083 | 2/1971 | Fournet et al. | 264/117 |
| 3,904,726 | 9/1975 | Jacquelin et al. | 264/117 |
| 3,927,194 | 12/1975 | Geller | 424/362 |

OTHER PUBLICATIONS

Chemical Abstracts, vol. 86 (1977), p. 161210j.
Chemical Abstracts, vol. 81 (1974), p. 54402y.
Markussen et al., Chem. Abstr. 88 #85230g (1978) of Ger. Off. 2,730,481, 12 Jan. 1978.

*Primary Examiner*—Shep K. Rose
*Attorney, Agent, or Firm*—Gordon W. Hueschen

[57] ABSTRACT

Cellulose granules suitable for use in tableting, having good flow and good binding characteristics, said granules having a particle size as follows:

less than five percent (5%) on a 35 mesh (Tyler) screen;
less than thirty percent (30%) through a 100 mesh screen; and
less than five percent (5%) through a 200 mesh screen, as measured on a Ro-Tap TM (Tyler) sifter using a 25 gram sample and with a sieving time of 25 minutes, said cellulose granules consisting essentially of compacted, granulated, and screened cellulose consisting essentially of cellulose fibers having an average length on their largest dimension of between about 20 and about 55 microns, especially between about 30 and about 40 microns, and process of making same by compacting, granulating, and classifying, preferably in a Chilsonator TM ; admixtures of said granules with pharmaceutical excipients or binders, especially dibasic calcium phosphate.

34 Claims, No Drawings

CELLULOSE FLOC GRANULES AND PROCESS

BACKGROUND OF INVENTION

1. Field of Invention

Cellulose granules suitable for use in tableting, especially by the direct compression method, having suitable flow characteristics and suitable binding characteristics to be useful for said purpose.

2. Prior Art

Flocked cellulose in the form of subdivided fibers or fiber fragments, having varying degrees of fiber characteristics, have found use in the pharmaceutical industry as binders and disintegrants in the making of pharmaceutical tablets. Such materials have found use in the two-stage process known as wet granulation, in which the various ingredients are first blended with a moistening liquid to form a pasty mass which is then sized through a coarse sieve. The wet granules are then dried and, if necessary, broken up again in a hammermill and resized to the desired mesh size of, for example, sixteen to thirty (16-30) mesh. The finished granules are then in a condition which permits adequate flow rates from the feed hopper to the tablet dies of a compressing machine.

Another approach to the manufacture of tablets is by the direct compression method, in which the ingredients are merely dry blended by simple admixture and then fed directly to tableting dies. This method offers substantial savings in time and equipment, but an absolute requisite for employment of this process is that all ingredients have a high order of fluidity. It is in this area of direct compression tablet production that previously-available flocked cellulose materials fall down. The previously-available materials fail to fulfill the three requisites for compression tablet making to an adequate extent. These requisites are as follows: The material must be free-flowing; it must have binding properties, and it must not stick to punches or dies. These requirements are taken from page fifteen of the text entitled "Tablet Making" by Arthur Little and K. A. Mitchell, Second Edition, The Northern Publishing Co., Ltd., Liverpool, England, 1968. Thus, since the previously-available flocked cellulose materials do not fulfill these requisites, it becomes necessary to find another form of cellulose which may be employed in the direct compression manufacture of tablets, which is free-flowing and particulate and still able to impart the necessary degree of binding to the tablet ingredients and, although imparting a certain requisite degree of hardness to the tablet, also permits the formed tablet to distintegrate at an adequate rate in aqueous or gastric solution. The problem is thus to provide a cellulose material of adequate fluidity and the means of transforming existing cellulose materials of an intransigent non-flowing fibrous nature into a form which flows readily, but without compromising its chemical nature by the addition of foreign matter such as gum or other binding agent. Thus, retention of the inherent characteristic of cellulose fibers to adhere tenaciously to each other, as by ordinary interfiber binding and hydrogen bonding, must be retained.

Such novel form of cellulose and method of producing the same are provided according to the present invention.

Of course, any cellulose material must meet additional requirements if it is to be used in pharmaceutical tableting; for example, all of the usual tests listed for Powdered Cellulose in the National Formulary, Volume XIV, page 786 and, if the end product is to be ingested by a human, then cellulose material must meet additional requirements as set forth in the Food Chemicals Codex, Third Supplement to the Second Edition, page 11. Such additional requirements are of course well known to one skilled in the art and go without saying, and form no part of the present invention, but will of course be included among the characteristics of the cellulose product of the invention if to be employed according to such high-requirement standards.

OBJECTS OF THE INVENTION

It is an object of the present invention to provide a novel cellulose material which is useful in tableting, especially compression tableting, which has good flow and binding characteristics and which is accordingly useful in said direct compression tableting whereas previously-available forms of cellulose were not. It is a further object of the invention to provide a method for obtaining such highly desirable form of cellulose. It is another object of the invention to provide such cellulose floc materials having the aforesaid desirable characteristics, in the form of granules having a specified particle size, by the compaction, granulation, and screening of cellulose fibers having an average length on their largest dimension between about twenty (20) and about fifty-five (55) microns, and preferably between about thirty (30) and about forty (40) microns. An additional object of the invention is the provision of such cellulose floc granules in admixture with a pharmaceutical excipient or binder, particularly dibasic calcium phosphate. A still further object of the invention is the provision of such cellulose floc granules by the employment of a Chilsonator TM. Other objects of the invention will become apparent hereinafter and still others will be apparent to one skilled in the art.

BRIEF DESCRIPTION OF THE INVENTION

Cellulose granules suitable for use in compression tableting, having good flow and good binding characteristics, of a suitable particle size for such employment, and consisting essentially of compacted, granulated, and screened cellulose consisting essentially of cellulose fibers having an average length on their largest dimension of between about twenty (20) and about fifty-five (55) microns, especially between about thirty (30) and about forty (40) microns, are provided according to the invention. Preferably, the cellulose is compacted between rolls under a pressure of 5,600–12,600 lbs./linear inch, especially 7,000–11,200 lbs./inch. Advantageously, the cellulose granules are admixed with a pharmaceutical excipient or binder, also in granular form, such as dibasic calcium phosphate, preferably up to about a 75/25 weight ratio, especially a 50/50 weight ratio. Conveniently, the compaction, granulation and sizing may be carried out in a Chilsonator TM device.

The process of the invention consists in the production of cellulose granules having a suitable particle size and consisting essentially of compacted, granulated and screened cellulose consisting essentially of cellulose fibers, by compacting cellulose by the application of pressure into a dense sheet of compacted cellulose, breaking the sheet up into granules of cellulose by granulation, and classifying the granules by passage through one or more sieves to yield the desired cellulose granules having the aforesaid suitable particle size. Preferably the cellulose fibers have an average length on their largest dimension of between about twenty (20) and about fifty-five (55) microns, and preferably the cellulose is compacted between rolls under a pressure of 5,600–12,600 lbs./linear inch, especially 7,000–11,200 lbs./linear inch. Advantageously, the compaction, granulation and sizing is carried out in a Chilsonator TM.

By provision of the cellulose granules of the present invention and the process for their production, all of the objects of the invention are fulfilled.

Apparatus Employed

Ro-Tap TM is the trademark for a sieving apparatus made by W. S. Tyler, Inc., 8200 Tyler Boulevard, Mentor, Ohio 44060.

The Tyler standard screen-scale sieves and their comparison with U.S. sieve series is to be found at page 963 of the "Chemical Engineer's Handbook", John H. Perry, Editor, Third Edition, published by McGraw-Hill Book Company, Inc. in 1950.

The Flo-Graph TM is the trademark for a device which can conveniently be employed for the measurement of flow properties or fluidity, produced by Austin Chemical Company, 5725 East River Road, Chicago, Ill. 60631. This apparatus is a commercially-available piece of equipment comprising a polished stainless-steel cone with an interior angle of fifty-eight degrees (58°), at the bottom of which is an orifice through which material flows into a receiver located on the platform of a recording device. Material to be tested is placed in the funnel and a recording is made of the rate of flow of the material through the orifice. Selection of an orifice diameter of three-eighths inch ($\frac{3}{8}$"), one-half inch ($\frac{1}{2}$"), or five-eighths inch ($\frac{5}{8}$") is made possible by means of a sliding orifice plate located in the botton of the cone. Provision is also made to allow the cone to be vibrated gently when necessary to aid flow. In this device, material having excellent fluidity and/or flow properties will flow rapidly and at a uniform rate through a small orifice without the necessity of providing the added impetus of vibration. Certain tests herein reported were made in a Flo-Graph TM apparatus set forth in the Examples.

The Chilsonator TM is an apparatus for the compaction, granulation, and sieving of material, which is a product of the Fitzpatrick Company, Elmhurst, Ill. Such equipment is advantageously employed according to the process of the present invention. Its further description and operation will appear elsewhere herein.

The Alpine Air Jet TM Sieve is a particularly advantageous sieving device, especially for relatively finely-divided materials, produced by Alpine A.G., 89 Ausburg 2, Federal Republic of Germany.

Starting Materials

Suitable starting materials for carrying out the process of the present invention and for production of the cellulose floc granules of the present invention are members of a family of fibrous and powdered cellulose materials produced by the Brown Company, of Berlin, N.H., and sold under their trademark Solka-Floc TM. Both food and pharmaceutical grades of this Solka-Floc TM product are available. Other cellulosic raw materials of similar nature and grade can of course also be employed. According to the invention the cellulose fibers of the starting cellulose floc material have an average length on their largest dimension of between about twenty (20) and about fifty-five (55) microns, advantageously between about thirty (30) and about forty (40) microns. Due to their toughness and resiliency, the fibers of this starting floc material do not undergo any essential change in these dimensions during processing according to the process of the present invention into the granular compositions of the invention.

Suitable cellulose floc and powder materials which can be employed as starting materials in the process of the invention and to make the cellulose floc granules of the present invention, and some of their characteristics, are set forth in Table I. As already stated, similar cellulose products having essentially the same properties and consisting essentially of cellulose fibers having an average length on their largest dimension of between about twenty (20) and about fifty-five (55) microns, preferably between about thirty (30) and about forty (40) microns, can be used equally as well as the Solka-Floc TM Brown Company products as set forth in Table I.

TABLE I

CHARACTERISTICS OF SOME REPRESENTATIVE STARTING CELLULOSE POWDERS*

The Solka-Floc TM ** products are pure, white, finely-divided cellulose fragments of natural cellulose fiber, made from highly purified wood pulp. The dry products are at least 99.5% cellulose, virtually lignin free, and have no relation to wood flour. Their pH value falls within a neutral range, and their brightness and color remain stable over extended periods. The sub-divided fibers or fiber fragments contain no obvious foreign material and have a slight, characteristic odor similar to standard. Grades BW-40 and BW-60 are slightly fibrous, and the remaining grades are relatively "free-flowing" powders.

The specified values of a number of properties listed below do not differ from one grade to another. The principal differences between grades are in bulk and in screen analysis.

| pH (10% suspension) | 5.0–7.5 |
|---|---|
| Loss on Drying, % | NMT 7 |
| Residue on Ignition, % | NMT 0.3 |
| Water-soluble Substances, % | NMT 1.5 |
| Heavy Metals, % | NMT 0.001 |
| Starch | Absent |

| | | Screen Analysis (Ro-Tap TM, Tyler) | | | Avg. Particle |
|---|---|---|---|---|---|
| Grade (NF) | Bulk (ml/gm) | On 35 mesh | Thru 100 mesh | Thru 200 mesh | Size (microns) |
| BW-40 | 3.0 ± 0.5 | LT 5 | NLT 70 | NLT 40 | 55–65 |
| BW-60 | 2.5 ± 0.3 | LT 1 | NLT 80 | NLT 45 | 45–55 |
| BW-100 | 2.0 ± 0.3 | LT 1 | NLT 85 | NLT 70 | 35–45 |
| BW-200 | 2.1 ± 0.1 | LT 0.5 | NLT 90 | NLT 75 | 30–40 |
| | | Screen Analysis (Alpine Air-Jet TM Sieve) | | | |
| | | Thru 200 mesh | Thru 400 Mesh | | |
| BW-300 | 2.2 ± 0.3 | NLT 99 | NLT 95 | | 15–25 |

* Fiber length is essentially unchanged in granules made therefrom.
** In Canada, sold as Alpha-Floc TM brand of powdered cellulose.

PROCESS AND PROCEDURE

In its simplest form, the process of the invention can be carried out by taking the starting cellulose floc and packing it under pressure into the form of a dense sheet. At first, this was done using a tablet-making die. Thereafter, the small sheet thus prepared was broken up, i.e. granulated by crushing, in its simplest form by means of a laboratory mortar and pestle. The produced granules are heterogeneous in size, and are therefore passed through sieves for preparing material of a more homogeneous nature. For manufacture of commercial quantities of cellulose floc granules, any suitable piece of apparatus may be employed. Any commercially-available production equipment which can carry out the successive steps of compaction, granulation, and sizing is suitable. A particularly suitable apparatus of this nature is available and has been found highly satisfactory for operations according to the present invention. This is the Chilsonator TM, made by the Fitzpatrick Company of Elmhurst, Ill. In this apparatus the cellulose floc is first compressed by being forcibly fed into the nip between two counter-rotating metal rolls. These rolls are hydraulically loaded so that extreme pressure can be exerted on the material in the nip. If the material can be compacted, a dense sheet of product issues from between the rolls. The sheet is then broken up in the granulator, which can also be fitted with a screen of any desired size. The granulated material is then classified by passage through one or more sieves to finally yield the cellulose floc granules of predetermined size. It has been found that a usable range of pressure in the nip of the Chilsonator TM rolls according to the invention is 5,600–12,600 lbs/linear inch, with the preferred range being 7,000–11,200 lbs./linear inch. With appropriate adjustment in the feed rate, pressure in the nip of the compacting rolls, intensity of granulation, size of post-granulation screens, and the like, it was found possible to employ numerous starting cellulose floc materials to product cellulose floc granules in the Chilsonator TM device.

DETAILED DESCRIPTION OF THE INVENTION

The following Examples are given by way of illustration only, and are not to be construed as limiting.

EXAMPLES 1–10a

Cellulose Floc Granules, Including Comparative Examples

Various grades of starting cellulose floc were subjected to pressures of 5,600–12,600 lbs./linear inch, preferably 7,000–11,200 lbs./linear inch, in a Chilsonator TM. The densely compacted sheet of cellulose floc was thereupon granulated in the Chilsonator TM and screened to give a particle size for the granules which was less than five percent (5%) on a thirty-five (35) mesh (Tyler) TM screen, less than thirty percent (30%) through a one hundred (100) mesh screen, and less than five percent (5%) through a two hundred (200) mesh screen as measured on a Ro-Tap TM sifter using a twenty-five (25) gram sample and sieving for twenty-five minutes. Granules meeting such specifications have been found to be of a practical and useful size for tablet formulation by direct compression.

The various grades of starting cellulose floc, after the said compaction, granulation, and sizing, were then subjected to testing in the Flo-Graph TM.

The results of the testing showed that finely-divided powdered cellulose, microcrystalline cellulose (Avicel PH-102 TM, F.M.C. Corporation) and certain other products and admixtures, were unsatisfactory from the standpoint of flow rate. The microcrystalline cellulose tested, although commonly used and well accepted in the pharmaceutical industry as an excipient or binder material, showed grossly inferior flow characteristics, either alone or in combination with other materials.

From this and other determinations, it was apparent that the cellulose floc granules having suitable flow characteristics for use in direct compression tableting were those having the desired particle size in which less than five percent (5%) were retained on a thirty-five (35) mesh Tyler screen, less than thirty percent (30%) passed through a one hundred (100) mesh Tyler screen, and less than five percent (5%) passed through a two hundred (200) mesh Tyler screen, when measured on a Ro-Tap TM (Tyler) sifter using a 25 gram sample and with a sieving time of twenty-five minutes, and which were prepared by the compaction, granulation, and screening of cellulose powder. Moreover, it was likewise apparent that the cellulose fibers in the starting powder and in the finished granules should have an average length on their longest dimension of between about twenty (20) and about fifty-five (55) microns, preferably between about thirty (30) and about forty (40) microns.

The relative flow rates of various materials according to the present invention and those included for comparison purposes are shown in Table II.

TABLE II

FLOW RATE OF CELLULOSE MATERIALS

| Sample | | Flow Rate in grams/sec. in Flo-Graph TM through orifice of given size | | |
|---|---|---|---|---|
| | | ⅜ inch | ½ inch | ⅝ inch |
| 1. | Solka-Floc TM BW-40 | X | X | X |
| 2. | BW-60 | X | X | X |
| 3. | BW-100 | X | X | X |
| 4. | BW-200 | X | X | X |
| 5. | BW-300 | X | X | X |
| 6. | Microcrystalline Cellulose (Avicel PH-102) TM | 5.2 | 3.4V | X |
| 7. | Sample 9 with equal weight of Avicel PH-102 TM | X | X | X |
| 8. | Sample 10 with equal weight of Avicel PH-102 TM | 9.5 | 4.8V | X |
| 9. | Granules from Solka-Floc TM BW-60 NF(45–55μ) | 8.9V | X | X |
| 10. | Granules from Solka-Floc TM BW-200 NF(30–40μ) | 12.6 | 8.7 | 4.0V |
| 10a. | Sample 10 with all particles finer than 100 mesh removed | 21.1 | 16.3 | 5.5 |

X = would not flow
V = vibration applied to funnel of flow test apparatus

EXAMPLE 11

Cellulose Floc Granules

The product BW-100 NF, consisting essentially of cellulose fibers having an average length on their largest dimension of between about thirty-five (35) and forty-five (45) microns, when compacted, granulated, and screened into cellulose powder having the prescribed dimensions resulted in cellulose floc granules which had an adequate rate of flow, somewhat less than the BW-200 NF granules, in grams/sec. through orifices of all sizes given, and was utilizable in the preparation of tablets having good binding characteristics, good dissolution characteristics in water and gastric fluid, a satisfactory degree of hardness, and adequate storage stability.

EXAMPLE 12

Cellulose Floc Granules

Cellulose floc granules made in the aforesaid manner from Solka-floc TM BW-300 NF were found to have adequate free-flowing properties at all orifice openings, but the granules and tablets produced therefrom were found to have relatively low structural integrity.

Accordingly, the minimum average length of the cellulose fibers has been set at about twenty (20) microns on their largest dimension to avoid the reduction in hardness exhibited in the granules and tablets produced from Solka-Floc TM BW-300 NF in which the cellulose fibers have an average length on their largest diameter between about fifteen (15) and about twenty-five (25) microns. Further loss of structural integrity, which might be encountered below twenty (20) microns, would of course be undesirable from the standpoint of utility of the cellulose floc granules in tablet making. At the other end of the scale, it is clear from the tests conducted that Solka-Floc TM BW-60 NF, consisting essentially of cellulose fibers having an average length on their largest dimension of between about forty-five (45) and fifty-five (55) microns, was definitely in the area of diminishing returns from the standpoint of flowability, so fifty-five (55) microns as an average length on the largest dimension of the cellulose fibers employed has been chosen as the upper limit. Cellulose floc granules prepared from Solka-Floc TM BW-40 NF, cellulose powder consisting essentially of cellulose fibers having an average length on their largest dimension of between about fifty-five (55) and about sixty-five (65) microns, were also produced in accord with the method of the invention, and found to exhibit poor flow rates in the Flo-Graph TM, another reason for setting the upper limit of criticality at about fifty-five (55) microns.

EXAMPLE 13

Cellulose Floc Granules

As an example of good flow through a one-half inch orifice of the Flo-Graph TM device without vibration, a sample of cellulose floc granules having the previously-disclosed sieve size specifications (roughly speaking, a product which passes through a thirty (30) mesh Tyler screen and is retained on a one hundred-fifty (150) mesh Tyler screen, designated by the number 30150) produced by compaction, granulation, and screening of cellulose powder consisting essentially of cellulose fibers having an average length on their largest diameter of between about thirty (30) and forty (40) microns, was tested in a test in which the flow was recorded over a period in excess of thirty (30) seconds. The flow rate was determined to be 8.7 grams/second, a rapid rate, and the flow was determined to be smooth.

EXAMPLE 14

Cellulose Floc Granules + Microcrystalline cellulose

In a further example designed to determine flow characteristics, the product of the preceding Example 13 was admixed in a ratio of 1 to 3 by weight with microcrystalline cellulose (Avicel PH-102) TM, and flow was determined on the Flo-Graph TM instrument using a one-half inch ($\frac{1}{2}''$) orifice and with vibration at fifteen (15) lbs./sq. inch. It was found that the mixture would not flow at all through the one-half inch ($\frac{1}{2}''$) orifice.

Tableting by Direct Compression

For tableting of the cellulose floc granules of the present invention according to the direct compression method, any suitable direct compression tableting device may be employed. The compressional force employed therein may range between 10,000 and 30,000 lbs./sq. inch, depending upon the equipment employed. Such equipment is well-known in the art and constitutes no part of the present invention. The tablets made from 100% cellulose floc granules according to the invention were found to disintegrate rapidly in water or in gastric fluid when tested according to normal testing procedure. They were also found to have adequate binding capacity and hardness, as well as tablet stability upon storage. The hardness of the tablets produced from cellulose floc granules alone without excipient or binder was found to be variable and could be increased by reducing the pressure employed during compaction and maintaining the pressure employed during tableting constant. Thus, softer granules as produced using less pressure during the compaction were found to give harder tablets when subjected to identical tableting conditions. The flow rate of the cellulose floc granules of the invention in the tableting procedure was adequate. It was generally excellent, especially when the granules were produced from cellulose fibers having an average length on their largest dimension of between about thirty (30) and about forty (40) microns. During the tablet-making operation, the cellulose floc granules of the invention were free-flowing, they had adequate binding properties for binding the tablet to itself, whether because of their innate hydrogen bonding capacity or inter-fiber bonding, and the cellulose floc granules did not stick to punches or dies during the tableting procedure. Moreover, as aforesaid, tablets produced therefrom gave satisfactory disintegration rates when tested according to standard procedure in water and gastric solutions, and exhibited adequate hardness characteristics as well as adequate storage stability properties.

Admixtures with pharmaceutical excipients and binders

In some cases, the cellulose floc granules of the present invention may advantageously be admixed with pharmaceutical excipients and/or binders. It is readily possible to prepare such blends of cellulose floc granules with such commonly-employed pharmaceutical excipients, adjuvants, and binders which normally find use in the art of tablet making. Such blends are produced by preparing an intimate blend of the cellulose floc granules with one or more other materials, also in granular form, as desired. If desired, further granulation or compaction, granulation and screening may be employed with the admixture. Blends can be made, for example, with substances such as microcrystalline cellulose, plain or chemically-modified starch, lactose, dextrose, mannitol, carboxymethyl cellulose, methyl cellulose, lubricants such as magnesium stearate or polyethylene glycols, or with mineral compounds commonly used as excipients such as dicalcium phosphate, silicon dioxide, talc, and the like. As one example of such blends as aforementioned, the cellulose floc granules may be blended with dibasic calcium phosphate ($CaHPO_4$). The dibasic calcium phosphate may be employed in any desired ratio with the cellulose floc granules, but a ratio of dibasic calcium phosphate to cellulose floc granules up to about a 75/25 weight ratio is preferred, and a 50/50 weight ratio may be used to advantage if desired.

However, any amount of a pharmaceutical excipient, adjuvant, or binder employed in admixture with the cellulose floc granules of the invention, or made into granules with the same, or admixed with the starting material for production of the cellulose floc granules of the invention, should not be employed at such levels as to reduce the necessary and desirable free-flow characteristics of the cellulose floc granules themselves. As noted, this percentage admixture must be carefully considered, inasmuch as some of the commonly-accepted excipients, such as microcrystalline cellulose, diminished the flow rate of the cellulose floc granules of the invention, as evidenced in Table II, Samples 6 through 8 and Example 14.

The granular pharmaceutical excipient, binder, or adjuvant is, as previously stated, generally also in granular form, and such materials which pass through a thirty (30) mesh screen and are retained on a sixty (60) mesh screen and containing only a few fines are commonly sold and are available for such purpose. Granular forms which pass through a twenty (20) mesh screen and are retained on a one hundred (100) mesh screen are somewhat coarser and may also be employed but not with the same advantage. The screen sizes mentioned are, as usual, the Tyler screen sizes, as set forth in the foregoing.

One advantage of admixture of the cellulose granules of the invention with pharmaceutical excipients or binders, particularly of a mineral nature, such as dibasic calcium phosphate, is an increase in the hardness of the tablet formed therefrom by direct compression. Using a standard tablet press, a blend of equal parts of granules according to the invention made from cellulose floc (Solka-Floc TM BW-60 NF) having an average fiber length between about forty-five (45) and fifty-five (55) microns, and calcium phosphate was prepared. The cellulose granules can be prepared independently and then admixed with the calcium phosphate granules, or the cellulose can be admixed with the calcium phosphate and then the granules prepared using a Chilsonator TM or otherwise in the manner set forth hereinbefore for the cellulose granules per se without additional pharmaceutical binder, adjuvant, or excipient.

A comparison of the tablets made from one hundred percent (100%) cellulose granules starting from Solka-Floc TM BW-60 NF and the tablets made from the aforesaid blend was made. The one hundred percent (100%) cellulose granule tablets disintegrated rapidly in water or in gastric fluid. These tablets had a hardness which was adequate but lower than desirable for maximum tablet stability. The hardness of the tablets prepared from the blend was greater and the disintegration rate in water or gastric fluid was not disadvantageously affected. The following Table III shows the results of the hardness test on two types of tablets.

TABLE III

HARDNESS OF TABLETS MADE FROM PURE CELLULOSE GRANULES AND FROM GRANULES CONTAINING 50% CELLULOSE AND 50% CaHPO₄

| Compressional Force (kgs./area)* | Hardness in Strong-Cobb Units | |
|---|---|---|
| | Cellulose Granules Alone | Cellulose + CaHPO₄ Granules |
| 520 | 1 | — |
| 1050 | 1 | 16 |
| 1570 | 2 | 24 |
| 2090 | 4 | — |

*Tablets made with 1.11 cm circular punch and die.

It was subsequently found that the hardness of tablets produced from cellulose granules alone could be considerably increased by reducing the pressure of the compaction, as in a Chilsonator TM, to the lower ranges, thereby producing softer granules which, when tableted, gave harder tablets without diminishing their disintegration rate in water or gastric fluids.

It is to be understood that the invention is not to be limited to the exact details of operation or exact compounds, compositions, methods, or procedures shown and described, as obvious modifications and equivalents will be apparent to one skilled in the art.

I claim:

1. A substantially dry process for producing cellulose granules having a particle size as follows:
   less than five percent (5%) on a 35 mesh (Tyler) screen;
   less than thirty percent (30%) through a 100 mesh screen;
   and less than five percent (5%) through a 200 mesh screen,
as measured on a sifter using a 25 gram sample and with a sieving time of 25 minutes, said cellulose granules consisting essentially of substantially dry compacted, granulated, and screened cellulose consisting essentially of cellulose fibers, which comprises the steps of substantially dry compacting cellulose powder or floc, wherein the cellulose fibers have an average length on their largest dimension of between about 20 and about 55 microns, by the application of pressure into a dense sheet of compacted cellulose, breaking the sheet up into granules of cellulose by substantially dry granulation, and classifying the granules by passage through one or more sieves to yield the desired cellulose granules having the aforesaid predetermined size ranges.

2. Process of claim 1, wherein the cellulose fibers have an average length on their largest dimension of between about 30 and about 40 microns.

3. Process of claim 1, wherein the cellulose is compacted under a pressure of 5600–12600 lbs/linear inch.

4. Process of claim 2, wherein the cellulose is compacted under a pressure of 7000–11200 lbs/linear inch.

5. Process of claim 1, wherein the cellulose granule product is admixed with a pharmaceutical excipient or binder.

6. Process of claim 2, wherein the cellulose granule product is admixed with a pharmaceutical excipient or binder.

7. Process of claim 1, wherein the cellulose granules are admixed with granular dibasic calcium phosphate.

8. Process of claim 7, wherein the cellulose granules are admixed with the dibasic calcium phosphate in an amount up to about a 75/25 weight ratio of dibasic calcium phosphate to cellulose.

9. Process of claim 8, wherein the cellulose granules are admixed with dibasic calcium phosphate in an amount of about a 50/50 weight ratio.

10. Process of claim 1, wherein the compaction, granulation and sizing is carried out in a single unitary apparatus.

11. Process of claim 1, wherein the cellulose is admixed with a pharmaceutical excipient or binder before compaction.

12. Process of claim 1, wherein the cellulose is admixed with a pharmaceutical excipient or binder after granulation.

13. Cellulose granules of claim 1, comprising also a pharmaceutical excipient or binder.

14. Cellulose granules suitable for use in tableting, having good flow and good binding characteristics, said granules having a particle size as follows:
    less than five percent (5%) on a 35 mesh (Tyler) screen;
    less than thirty percent (30%) through a 100 mesh screen;
    and less than five percent (5%) through a 200 mesh screen,
as measured on a sifter using a 25 gram sample and with a sieving time of 25 minutes, said cellulose granules consisting essentially of compacted, granulated, and screened cellulose powder or floc, produced in accord with the substantially dry process of claim 1, and consisting essentially of cellulose fibers having an average length on their largest dimension of between about 20 and about 55 microns.

15. Granules of claim 14, wherein the cellulose fibers have an average length on their largest dimension of between about 30 and about 40 microns.

16. Granules of claim 4, wherein the cellulose is compacted under a pressure of 5600–12600 lbs/linear inch.

17. Granules of claim 15, wherein the cellulose is compacted under a pressure of 7000–11200 lbs/linear inch.

18. Granules of claim 14, comprising in admixture therewith a pharmaceutical excipient or binder.

19. Granules of claim 15, comprising in admixture therewith a pharmaceutical excipient or binder.

20. Granules of claim 14, comprising in admixture therewith granular dibasic calcium phosphate.

21. Granules of claim 20, wherein the ratio of dibasic calcium phosphate to cellulose is up to about a 75/25 weight ratio.

22. Granules of claim 21, wherein the dibasic calcium phosphate and cellulose are present in about a 50/50 weight ratio.

23. Granules of claim 14, wherein the compaction, granulation and sizing is carried out in a single unitary apparatus.

24. A tablet produced by the essentially dry direct-compression of cellulose granules according to claim 14.

25. A tablet produced by the essentially dry direct-compression of cellulose granules according to claim 15.

26. A tablet produced by the essentially dry direct-compression of cellulose granules according to claim 16.

27. A tablet produced by the essentially dry direct-compression of cellulose granules according to claim 17.

28. A tablet produced by the essentially dry direct-compression of cellulose granules according to claim 18.

29. A tablet produced by the essentially dry direct-compression of cellulose granules according to claim 19.

30. A tablet produced by the essentially dry direct-compression of cellulose granules according to claim 20.

31. A tablet produced by the essentially dry direct-compression of cellulose granules according to claim 21.

32. A tablet produced by the essentially dry direct-compression of cellulose granules according to claim 22.

33. A tablet produced by the essentially dry direct-compression of cellulose granules according to claim 23.

34. A tablet produced by the essentially dry direct-compression of cellulose granules according to claim 13.

* * * * *

UNITED STATES PATENT AND TRADEMARK OFFICE
CERTIFICATE OF CORRECTION

PATENT NO. : 4,269,859

DATED : May 26, 1981

INVENTOR(S) : Erwin E. Morse

It is certified that error appears in the above—identified patent and that said Letters Patent is hereby corrected as shown below:

[56] References Cited, under OTHER PUBLICATIONS, line 3, "Markussen et al."; "#85230g" should read -- #85230q --

Col. 2, line 7; "saving" should read -- saying --

Col. 3, line 34; "botton" should read -- bottom --

Col. 10, line 39 (line 13 & 14 of Claim 1); "of substantially dry compacting cellulose" should read -- of compacting substantially dry cellulose --

Col. 11, line 37 (line 1 of Claim 16); "4" should read -- 14 --

Signed and Sealed this

Twenty-second Day of September 1981

[SEAL]

Attest:

GERALD J. MOSSINGHOFF

Attesting Officer

Commissioner of Patents and Trademarks

UNITED STATES PATENT AND TRADEMARK OFFICE
CERTIFICATE OF CORRECTION

PATENT NO. : 4,269,859
DATED : May 26, 1981
INVENTOR(S) : Erwin E. Morse

It is certified that error appears in the above—identified patent and that said Letters Patent is hereby corrected as shown below:

Col. 11, line 13 (claim 13, line 1); "claim 1" should read -- claim 14 --

Signed and Sealed this

Twenty-fifth Day of October 1983

[SEAL]

Attest:

GERALD J. MOSSINGHOFF

Attesting Officer    Commissioner of Patents and Trademarks